United States Patent [19]  [11] 3,962,265
Johnston  [45] June 8, 1976

[54] H'-(4-((6-CHLORO-2-PYRIDINYL)OXY)PHENYL)-N-METHYL-N-(1-METHYL-2-PROPYNYL)UREA

[75] Inventor: Howard Johnston, Walnut Creek, Calif.

[73] Assignee: The Dow Chemical Company, Midland, Mich.

[22] Filed: Apr. 21, 1975

[21] Appl. No.: 570,067

Related U.S. Application Data

[63] Continuation of Ser. No. 435,619, Jan. 22, 1974, abandoned.

[52] U.S. Cl. ............... 260/295 E; 260/294.8 H; 260/294.9; 260/295.5 D; 71/92; 71/94
[51] Int. Cl.² ...................................... C07D 213/86
[58] Field of Search ............... 260/294.8 H, 294.9, 260/295 E, 295.5 D; 71/92, 94

[56] References Cited
UNITED STATES PATENTS
3,701,807  10/1972  Chupp ........................... 260/553 A Primary Examiner—Alan L. Rotman
Attorney, Agent, or Firm—S. Preston Jones; Gary D. Street; C. Kenneth Bjork

[57] ABSTRACT

Disclosed are novel substituted pyridinyloxy-(thio)phenyl alkenyl- and alkynyl urea compounds and N-oxide derivatives thereof. The compounds of the present invention are useful as herbicides and can be formulated to provide herbicidal compositions.

1 Claim, No Drawings

N'-(4-((6-CHLORO-2-PYRIDINYL)OXY)PHENYL)-N-METHYL-N-(1-METHYL-2-PROPYNYL)UREA

CROSS-REFERENCE TO RELATED APPLICATION

This is a continuation of application Ser. No. 435,619 filed Jan. 22, 1974, now abandoned.

SUMMARY OF THE INVENTION

The present invention is directed to substituted pyridinyloxy(thio)phenyl alkenyl- and alkynyl urea compounds corresponding to the formula:

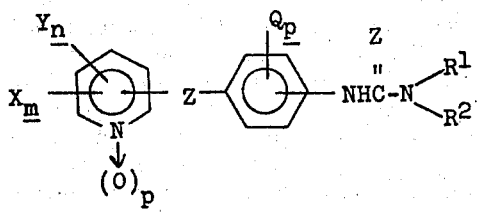

wherein:
each $p$ independently represents an integer of 0 or 1;
each X independently represents bromo, chloro, iodo or fluoro;
$m$ represents an integer of 0 to 4, inclusive;
each Y independently represents cyano, nitro, $ZR^3$, $-C(R)_3$ or

$n$ represents an integer of 0 to 2, inclusive;
each Z independently represents oxygen or sulfur;
Q represents methyl, ethyl, halo, nitro, cyano or trifluoromethyl;
each R independently represents hydrogen or halo;
$R^1$ represents hydrogen, methyl or ethyl;
$R^2$ represents an alkenyl group containing from two to about six carbon atoms or an alkynyl group containing from about three to about six carbon atoms;
$R^3$ represents an alkyl group of from 1 to about 3 carbon atoms, and
$R^4$ and $R^5$ each independently represents hydrogen or an alkyl group of from 1 to about 4 carbon atoms.

For the sake of brevity and simplicity, the term "active ingredient" is used hereinafter in this sepcification to broadly describe the compounds of the present invention. In the reaction sequences set forth below, all substitutents, unless otherwise expressly indicated, are the same as set forth above.

The active ingredients of the present invention are normally crystalline solids and are soluble in the usual organic solvents, as well as having some solubility in water. The active ingredients are useful as plant growth regulants, and especially as herbicides when applied either as a pre-emergence or post-emergence treatment and may be formulated with the usual herbicide carriers for use in controlling unwanted plants.

DETAILED DESCRIPTION

The active ingredients of the present invention are useful as herbicides, particularly as post-emergent herbicides. Certain of the active ingredients of the present invention have been found suitable for controlling unwanted plants among crops such as, for example, soybeans, corn, wheat and rice, without injuring the crops. As used in the present specification and claims, the term "herbicide" means an active ingredient which, when used in a growth controlling amount, controls or modifies the growth of plants. By a "growth controlling amount" is meant an amount of compound which causes a modifying effect upon the growth of plants. Such modifying effects include all deviations from natural development, for example, killing, retardation, defoliation, desiccation, regulation, stunting, tillering, and the like. By "plants" it is meant germinant seeds, emerging seedlings, and established vegetation, including the roots and above-ground portions.

The term "alkyl", unless otherwise expressly designated, is used herein and in the appended claims to designate a straight or branched chain alkyl radical containing from 1 to about 4 carbon atoms, such as, for example, methyl, ethyl, propyl, isopropyl, butyl, isobutyl and tertbutyl. The term "alkoxy", as represented by the radical $ZR^3$, includes straight or branched-chain radicals containing from 1 to about 4 carbon atoms, such as, for example, methoxy, ethoxy, propoxy, isopropoxy, butoxy, isobutoxy and tert-butoxy.

The terms "halo" and "halogen" are employed herein to represent chlorine, fluorine and bromine. The term "alkenyl" as employed in the present specification and claims designates an alkenyl radical containing from 2 to about 6 carbon atoms, such as, for example, ethenyl, propenyl, 2-methylpropenyl, butenyl, pentenyl, hexenyl and the like. The term "alkynyl" as used herein and in the appended claims designates an alkynyl radical containing from 3 to about 6 carbons, such as, for example, propynyl, 2-methylpropynyl, butynyl, pentynyl, hexynyl and the like. Preferred compounds of the present invention are those compounds wherein $n$ is 0 and $m$ is at least 1. In a further preferred embodiment, $m$ is 0 and $n$ is at least 1. Another preferred class of compounds are those wherein the sum of $m + n$ is one and X or Y is ring substituted in the 6-ring position of the pyridine moiety. In another embodiment, those compounds wherein the sum of $m + n$ is at least two are preferred. In an additional preferred embodiment, $R^1$ is methyl or ethyl and $R^2$ is alkenyl. In still another preferred embodiment, $R^1$ is methyl or ethyl and $R^2$ is alkynyl. In a further embodiment, compounds wherein $n$ is 0 and $m$ is at least 1, X is ring substituted in the 6-ring position, $R^1$ is methyl or ethyl and $R^2$ is alkynyl are preferred.

The active ingredients of the present invention, conveniently hereinafter referred to as "phenylurea" compounds, are prepared by reacting a selected substituted pyridinyloxy(thio)phenyl iso(thio)cyanate reactant (hereinafter, "isocyanate" reactant) with a selected substituted amino -alkene or -alkyne reactant in the presence of an inert solvent carrier. The reaction can be illustrated as follows:

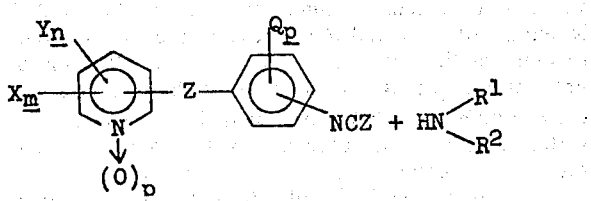

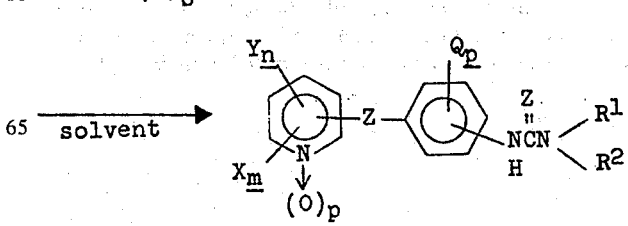

Reaction I

In the above and following illustrative reaction sequences, all substituents are as previously defined. The above reaction sequence is conducted under ambient atmospheric pressures and at ambient temperatures, usually from about 20° to about 50°C. The reactants are usually employed in about equimolar amounts and are ordinarily contacted in the presence of an inert solvent carrier, such as, for example, benzene, toluene, pyridine or the like. In usual procedures, the selected amino-alkene or -alkyne reactant is added, portionwise, to the isocyanate reactant in the solvent carrier. The resulting reaction mixture is stirred at ambient temperatures with a small amount of an actuating agent, such as triethylamine. The reaction is ordinarily carried to substantial completion after a period of from about ½ to about 16 hours. The product precipitate formed in the reaction mixture during the reaction is recovered by filtration, washed with a solvent, such as, for example, hexane or the like, and dried. The product thus obtained can be further purified by dissolving the same in a solvent, such as, for example, boiling benzene, filtering the resulting solution and then removing the solvent by evaporation. The product residue, usually an oil, is mixed with n-hexane to obtain the purified product as a crystalline solid.

The isocyanate intermediates, with the exception of the N-oxide derivatives thereof, can be obtained according to the following illustrative reaction sequence:

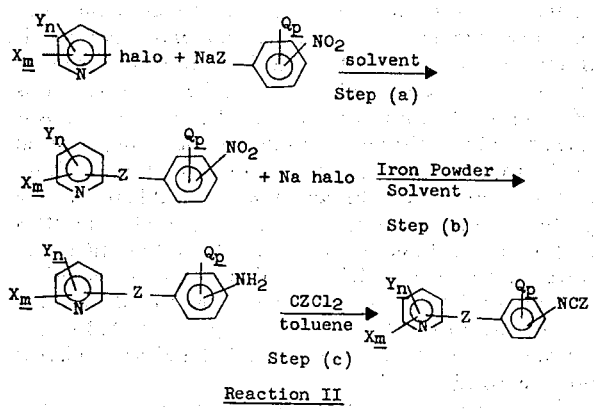

Reaction II

The reaction in step (a) of Reaction II proceeds readily under ambient atmospheric pressure at reaction temperatures of from about 100° to about 160°C. for a period of from about 3 to about 5 hours. In such operations, a salt of the substituted nitro(thio)phenol, prepared by mixing stoichiometric amounts of the same with a base, such as sodium hydroxide or sodium metal in methanol, is mixed with the selected halopyridine reactant in the presence of an inert solvent, such as previously mentioned with respect to Reaction I, and the resulting reaction mixture heated at a temperature within the above-indicated ranges. Following the substantial completion of the reaction, the reaction mixture is cooled and mixed with cold water. The resulting product precipitate is recovered by filtration and recrystallized according to conventional techniques from a solvent, such as, for example, benzene, methylene chloride and the like.

The product thus obtained from step (a) of Reaction II is mixed, in the presence of an aqueous alcohol solution, with a reducing agent, such as, for example, iron powder. The resulting reaction mixture is heated to the reflux temperature thereof with vigorous stirring and an alcohol solution of concentrated hydrochloric acid is added thereto, portionwise, over a 10 to 30 minute period. The reaction mixture is then heated at the reflux temperature for a period of from about 2 to about 4 hours and then filtered while hot. The solid product thus obtained is washed with an aqueous alkanol solution, such as 50–95% ethanol, and the filtrate portions combined and extracted with a solvent such as benzene, methylene chloride or the like. The extract is then dried, treated with activated charcoal, such as Norite, filtered and evaporated to dryness to obtain the desired pyridinyloxy(thio)benzenamine intermediate as a crystalline solid or oily liquid.

The isocyanate intermediates are readily prepared according to step (c) above by first preparing a solution of phosgene or thiophosgene in a solvent such as, for example, water, toluene or the like, and then rapidly adding, with stirring, a solution of the benzenamine intermediate in toluene. The benzenamine addition is regulated so as to maintain the temperature of the mixture at about 5°C. or less, with additional quantities of solvent being added if necessary. Following the completion of the benzenamine addition, the reaction mixture is agitated and heated gradually until a temperature of from about 75° to about 95°C. is reached. The solvent carrier is then removed from the reaction mixture by evaporation under reduced pressure and the remaining residue taken up in hexane which is then cooled to crystallize the desired product. An excess of phosgene or thiophosgene, in a ratio of from about 3 to about 4 moles thereof per mole of amine reactant, is preferably employed in the reaction. During the reaction, excess phosgene can be removed by purging the reaction mixture withh an inert gas, such as nitrogen.

The N-oxide derivatives of the above isocyanate intermediates are usually prepared by another method in view of the high reactivity of the N-oxide ( =N→ 0) group with certain reagents, such as reducing agents employed in step (b) of Reaction II. In such method, the salt of a selected substituted nitro(thio)phenol reactant of the above formula is reduced to the corresponding amino(thio)phenol reactant with a reducing agent according to the procedures in step (b) of Reaction II. The thus-formed amino(thio)phenol reactant is then reacted with the N-oxide derivative of a selected substituted halopyridine reactant to obtain the N-oxide form of the desired pyridinyloxy(thio)benzenamine intermediate. The latter reaction is carried out employing procedures analogous to those employed in step (a) of Reaction II. The benzenamine intermediate can then be reacted with phosgene or thiophosgene according to step (c) of Reaction II to obtain the desired N-oxide derivatives of the pyridinyloxy(thio)-phenyliso(thio)-cyanate intermediates employed in Reaction I.

In still other procedures, the foregoing amino(thio)-phenol reactant can be reacted with phosgene or thiophosgene, as in step (c) of Reaction II, to obtain a corresponding phenyliso(thio)cyanate reactant which is reacted with a selected substituted alkene- or alkyne-amino reactant as in Reaction I to obtain a corresponding N-alkenyl- or alkynyl-N-'-(hydroxy- or mercapto-phenyl)urea reactant. The latter phenylurea reactant can be reacted with an N-oxide halopyridine reactant in the presence of a base, such as, for example, sodium hydroxide or sodium metal in methanol, and a solvent carrier, such as previously mentioned herein, at temperatures ordinarily ranging from about 20° to about 80°C. for a period generally from about 1 to about 6 hours to obtain the desired active ingredients of the present invention. The desired product is recovered in a similar manner to the recovery procedures set forth hereinabove.

The N-oxide derivatives of the halopyridine reactants employed above as starting materials are prepared according to conventional oxidative procedures. In typical known types of operations, the selected halopyridine reactant is treated with anhydrous trifluoroacetic acid and excess 90% hydrogen peroxide under reflux conditions to obtain the desired N-oxide derivative.

The following example illustrates the present invention and the manner by which it can be practiced but, as such, should not be construed as a limitation upon the overall scope of the same.

EXAMPLE 1

N'-(4-((6-chloro-2-pyridinyl)oxy)phenyl)-N-methyl-N-(1-methyl-2-propynyl)urea

N'-(4-((6-chloro-2-pyridinyl)oxy)phenyl)isocyanate (7.0 grams; 0.028 mole) was mixed with 50 milliliters (ml) of benzene and 3-methylamino-1-butyne (2.02 grams; 0.024 mole) added thereto with stirring in portions over a period of about 5 minutes. The resulting reaction mixture was stirred at ambient temperatures for about ten minutes and about 5–6 drops of triethylamine added thereto, with the reaction mixture temperature increasing to about 33°C. The reaction mixture was then maintained at ambient temperatures with stirring for a period of about 15 hours. Following the reaction period, the reaction mixture was filtered to recover the precipitate formed during the reaction and the recovered product precipitate washed with hexane and dried. The product was further purified by dissolving the same in boiling benzene, filtering the resulting solution while hot and then removing the solvent by evaporation. The light tan oil residue thus obtained was stirred with n-hexane and the solution cooled to obtain the desired title product as a white crystalline solid having a melting point of 140°–142.5°C.

Other pyridinylurea compounds and derivatives are similarly prepared from selected substituted isocyanate intermediates in accordance with the procedures of the foregoing Example and the foregoing teachings of the specification. Such other compounds include, inter alia, the following:

N-ethenyl-N'-(4-((3,5,6-trichloro-2-pyridinyl)-oxy)-phenyl)-N-methylurea;

N'-(4-((6-methoxy-2-pyridinyl)oxy)phenyl)-N-ethyl-N-(1-methyl-2-pentenyl)urea;

N'-(4-((6-fluoro-4-pyrimidinyl)oxy)phenyl)-N-methyl-N-(3-hexenyl)urea;

N-(3-butenyl)-N'-(4-((6-bromo-2-pyridinyl)oxy)-phenyl)thiourea;

N'-(4-((6-iodo-2-pyridinyl)thio)-3-chlorophenyl)-N-methyl-N-(1-methyl-3-butenyl)urea;

N-(3-butynyl)-N'-(4-((3,4,5,6-tetrachloro-2-pyridinyl)oxy)-3-methylphenyl)urea;

N-butynyl-N'-(4-((3,4,5,6-tetrabromo-2-pyaidinyl)thio)-3-cyanophenyl)-N-methylthiourea;

N-(5-hexynyl)-N-(4-((6-(trifluoromethyl)-4-pyridinyl)thio)-3-nitrophenyl)-N-methylurea;

N-(5-hexenyl)-N-(3-((6-chloro-4-(trifluoromethyl)-2-pyridinyl)oxy)-3-(trifluoromethyl)phenyl)-N-methylurea;

N-ethenyl-N'-(4-((pyridinyl)oxy)phenyl)-N-methylurea;

N'-((4-(6-cyano-4-pyridinyl)thio)phenyl)-N-methyl-N-(1-methyl-2-propenyl)urea;

N'-(4-((4,5-dichloro-6-fluoro-2-pyridinyl)oxy)-phenyl)-N-methyl-N-(1-methyl-2-propynyl)thiourea;

N-(2-propenyl)-N'-(4-((4,6-bis(trifluoromethyl)-2-pyridinyl)oxy)phenyl)-N-methylthiourea;

N'-((3-(2-pyridinyl)thio)phenyl)-N-methyl-N-(1-methyl-3-butynyl)urea;

N-(2-butenyl)-N'-(4-((3-pyridinyl)oxy)phenyl)-N-methylurea;

N-(2-butynyl)-N'-(4-((6-nitro-3-pyridinyl)oxy)-phenyl)urea;

N'-(4-((6-(methylthio)-2-pyridinyl)oxy)phenyl)-N-methyl-(1-methyl-2-propenyl)urea;

N'-(4-((6-methyl-4-pyridinyl)oxy)phenyl)-N-ethyl-N-(3-propenyl)urea;

N'-(4-((6-chloro-4-cyano-2-pyridinyl)thio)phenyl)-N-(3-butenyl)-N-methylurea;

N-(3-butenyl)-N'-(4-((6-chloro-4-(trifluoromethyl)-2-pyridinyl)oxy)phenyl)-N-methylurea;

N-(2-propynyl)-N'-(4-((6-(propylthio)-2-pyridinyl)oxy)phenyl)-N-methylthiourea;

N'-(4-((4-isopropoxy)-2-pyridinyl)oxy)phenyl)-N-methyl-N-(5-hexynyl)thiourea;

N'-(4-((6-chloro-5-(chlorodifluoromethyl)-2-pyridinyl)oxy)phenyl)-N-methyl-N-(1-methyl-2-propynyl)-thiourea;

N-(3-butenyl)-N'-(3-((4-chloro-6-amino-2-pyridinyl)oxy)phenyl)-N-methylurea;

N'-(3-((2,6-dicyano-2-pyridinyl)oxy)-4-ethyl-phenyl)-N-(1-methyl-3-butynyl)urea;

N'-(5-((4-bromo-6-methylamino-2-pyridinyl)thio)-3-bromophenyl)-N-methyl-(3-pentynyl)thiourea;

N-(4-pentenyl)-N'-(3-((5-(dichloromethyl)-2-pyridinyl)oxy)-4-cyanophenyl)-N-methylurea;

N'-(4-((5-methyl-4,6-dichloro-2-pyridinyl)thio)-3-methylphenyl)-N-methyl-N-(1-methyl-2-pentynyl)urea;

N'-(4-((4,6-dimethyl-5-chloro-2-pyridinyl)oxy)-3-fluorophenyl)-N-methyl-N-(2butynyl)thiourea;

N-(4-((4,6-dinitro-3-pyridinyl)oxy)phenyl)-N-methyl-N-(2-propynyl)urea;

N-(4-((5-chloro-4,6-dimethoxy-2-pyridinyl)oxy)-3-chlorophenyl)-N-ethyl-N-(4-hexynyl)thiourea;

N'-(4-((6-bromo-4-n-butylamino-2-pyridinyl)-thio)-3-(trifluoromethyl)phenyl)-N-methyl-N-(3-butenyl)-urea;

N'-(3-((2-di-n-butylamino-5 -methyl-4-pyridinyl)-oxy)phenyl)-N-(3-butynyl)urea;

N'-(4-((4,6-diamino-5-chloro-2-pyridinyl) 1-methyl-2-propynyl)urea;

N'-(5-((6-chloro-3,5-dinitro-2-pyridinyl)thio)-3-methylphenyl)-N-2-propynylurea;

N'-(4-((2,6-bis(trifluoromethyl)-4-pyridinyl)-oxy)-N-methyl-N-(3-pentynyl)urea;

N'-(4-((5,6-dichloro-4-(difluoromethyl)-2-pyridinyl)oxy)phenyl)-N-methyl-N-(3-butynyl)urea;

N'-(4-((2,6-di-(dimethylamino)-4-pyridinyl)-thio)-phenyl)-N-methyl-N-(5-hexynyl)urea; and N'-(4-((2-cyano-6-(trifluoromethyl)-4-pyridinyl)-thio)phenyl)-N-(1-methyl-2-propynyl)urea.

The benzenamine and isocyanate intermediates employed are readily apparent in view of the foregoing enumerated compounds. Such benzenamine intermediates are of the formula represented in Reaction Sequence II of the specification and are prepared in accordance with the teachings of the specification. The nomenclature for such intermediates, for example, the corresponding benzenamine intermediate of the compound of Example 1, would be N'-(4-((6-chloro-2-pyridinyl)-oxy)phenyl)benzenamine. The isocyanate intermediates employed to prepare the pyridinylurea compounds are likewise readily apparent in veiw of the foregoing enumerated compounds. Such isocyanate intermediates correspond to the general formula represented in reaction sequence II set forth hereinbefore and are prepared according to the teachings set forth in the specification. Other benzenamine and isocyanate intermediates are similarly prepared and named.

The compounds of the present invention have been found to be suitable for use in methods for the pre- and post-emergent control of weeds or other unwanted vegetation. Certain of the active ingredients of the present invention have been found to be active against undesired vegetation in the presence of desired crop plants while producing only a negligible effect on the crop plants. For all such uses, unmodified active ingredients of the present invention can be employed. However, the present invention embraces the use of a herbicidally-effective amount of the active ingredients in composition form with a material known in the art as an adjuvant or carrier in solid or liquid form. Thus, for example, an active ingredient can be dispersed on a finely divided solid and employed therein as a dust. Also, the active ingredients, as liquid concentrates or solid compositions comprising one or more of the active ingredients, can be dispersed in water, typically with the aid of a wetting agent, and the resulting aqueous dispersion employed as a spray. In other procedures, the active ingredient can be employed as a constituent of organic liquid compositions, oil-in-water and water-in-oil emulsions, or water dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

As organic solvents used as extending agents there can be employed hydrocarbons, e.g. benzene, toluene, xylene, kerosene, diesel fuel, fuel oil, and petroleum naphtha, ketones such as acetone, methylethylketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing them in air by means of a compressed gas such as dichlorodifluoromethane or trichlorofluoromethane and other Freons and Genetrons, for example.

The active ingredients of the present invention can also be applied with adjuvants or carriers such as talc, pyrophyllite, synthetic fine silica, attapulgus clay, keiselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (nonionic 218), long chain ethylene oxidepropylene oxide condensation products, e.g., Pluronic 61 (molecular weight 1000), polyethylene glycol ester of tall oil acids, sodium octyl phenoxyethoxyethyl sulfate, tris(polyoxyethylene)sorbitan monostearate (Tween 60), and sodium dihexyl sulfosuccinate.

The concentration of the active ingredients in liquid compositions generally is from about 0.003 to about 95 percent by weight or more. Concentrations of from about 0.003 to about 50 weight percent are often employed. In dusts or dry formulations, the concentration of the active ingredient can be from about 0.003 to about 95 weight percent or more; concentrations of from about 0.003 to about 50 weight percent are often conveniently employed. In compositions to be employed as concentrates, the active ingredient can be present in a concentration of from about 5 to about 98 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of power-dusters, boom and hand sprayers, spray-dusters, by addition to irrigation water, and by other conventional means. The compositions can also be applied from airplanes as a dust or a spray because they are effective in very low dosages.

The exact dosage to be applied is dependent not only upon the specific active ingredient being employed, but also upon the particular plant species to be modified and the stage of growth thereof, as well as the part of the plant to be contacted with the toxic active ingredient. Thus, it is to be understood that all of the active ingredients of the invention and compositions containing the same may not be equally effective at similar concentrations or against the same plant species. In non-selective pre-emergence and foliage treatments the compositions of this invention are usually applied at an approximate rate of from about 1 to about 25 lbs. per acre, but lower or higher rates may be appropriate in some cases. In selective post-emergence operations to foliage, an application rate of from about 0.16 to about 5.0 pounds per acre can be employed. In some instances, lower rates may be utilized while higher rates may be necessary, in other instances. In view of the foregoing and following disclosures, one skilled in the art can readily determine the optimum rate to be applied in any particular case.

So as to illustrate the general and selective phytotoxic properties of the active ingredients of the present invention, a group of controlled greenhouse experiments is described below.

In pre-emergence operations, seeds of selected species are planted in seedbeds and, while exposed, sprayed with a given volume of a solution containing a predetermined amount of the candidate active ingredient to provide the dosage rate desired. Such compositions are prepared by mixing the selected active ingredient and an emulsifier or dispersant with water. The seeds are then covered with a layer of soil maintained under conditions conducive to growth. A portion of the planted seedbeds are left untreated to provide controls for comparative purposes. All seedbeds are watered as needed. About 14 days after seeding and treating, the effect of each test ingredient on the seeds is evaluated by a comparison with the control seedbeds.

In post-emergence operations, various species of plants are seeded in beds of good agricultural soil. After the plants have emerged and grown to a height of from about 2 to about 6 inches, certain of the plants are sprayed to run-off with a given volume of a composition prepared as set forth above. Other plants are left untreated to provide comparative controls. All plants are maintained as above for a period of about 14 days and then evaluated to determine the effect of the test ingredient.

In representative pre-emergence operations, the N'-(4-((6-chloro-2-pyridinyl)oxy)phenyl)-N-methyl-N-(1-methyl-2-propynyl)urea compound was found to give complete control of the growth of the seeds of German millett, barnyard grass, crabgrass, pigweed and velvet leaf species at an application rate of about ten pounds per acre.

In representative post-emergence operations, the N'-(4-((6-chloro-2-pyridinyl)oxy)phenyl)-N-methyl-N-(1-methyl-2-propynyl)urea compound was found to give complete control of the growth of German millett, barnyard grass, crabgrass, wild oat, pigweed, bindweed, velvet leaf and annual morning glory plants at an application rate of about ten pounds per acre.

In other selective post-emergence operations, the N'-(4-((6-chloro-2-pyridinyl)oxy)phenyl)-N-methyl-N-(1-methyl-2-propynyl)urea compound was found to give from substantial (90%) to complete control of the growth of German millett, barnyard grass, crabgrass, pigweed, bindweed and velvet leaf plants at an application rate of about 0.16 pounds per acre with little or no inhibition of the growth of corn, rice, wheat and soybean plants.

The substituted amino -alkene and -alkyne, halopyridine, nitro(thio)phenol and carbamoyl halide reactants employed to prepare the compounds of the present invention are either readily available or can be prepared by those skilled in the art according to procedures which are known or are analogous to those set forth in the open literature.

Although the invention is described with respect to specific embodiments and modifications, the details thereof are not to be construed as limitations except to the extent indicated in the following claims.

I claim:

1. The compound which is N'-(4-((6-chloro-2-pyridinyl)oxy)phenyl)-N-methyl-N-(1-methyl-2-propynyl)urea.

* * * * *

UNITED STATES PATENT AND TRADEMARK OFFICE
CERTIFICATE OF CORRECTION

PATENT NO. : 3,962,265
DATED : June 8, 1976
INVENTOR(S) : Howard Johnston

It is certified that error appears in the above-identified patent and that said Letters Patent are hereby corrected as shown below:

Title and Abstract page, Item [54], first line,
"H'-(4-((6-CHLORO-2-" should read -- N'-(4-((6-CHLORO-2- --.

Column 1, line 1, same error as above, "H" should read -- N --.

Column 1, line 47, "sepcification" should read
-- specification --.

Column 1, line 50, "substitutents" should read
-- substituents --.

Column 4, line 42, "withh" should read -- with --.

Column 6, line 7, "2-pyaidinyl)-" should read -- 2-pyridinyl --.

Column 6, line 57, "(2butynyl)thiourea" should read
-- (2-butynyl)thiourea --.

Column 6, line 67, after "pyridinyl)" insert omitted portion
of compound name; namely, -- oxy)phenyl)-N-methyl-( --

Signed and Sealed this

First Day of February 1977

[SEAL]

Attest:

RUTH C. MASON
*Attesting Officer*

C. MARSHALL DANN
*Commissioner of Patents and Trademarks*